US00PP36749P2

(12) United States Plant Patent
Nir

(10) Patent No.: US PP36,749 P2
(45) Date of Patent: Jun. 17, 2025

(54) ***CHAMELAUCIUM* PLANT NAMED 'ARBEL'**

(50) Latin Name: *Chamelaucium uncinatum*
Varietal Denomination: ARBEL

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 18/620,014

(22) Filed: Mar. 28, 2024

(51) Int. Cl.
*A01H 5/02* (2018.01)
*A01H 6/00* (2018.01)

(52) U.S. Cl.
USPC ..... Plt./229

(58) Field of Classification Search
USPC ..... Plt./229
CPC ..... A01H 5/02; A01H 5/00; A01H 6/00
See application file for complete search history.

(56) References Cited

PUBLICATIONS

Club Global Flowers 2023 *Chamelaucium uncinatum* 'Arbel' retrieved on Jul. 30, 2024 at https://club.global.flowers/en/chamelaucium/7048-chamelaucium-uncinatum-arbel, 3 pp. (Year: 2023).*
Community Plant Variety Office CPVO Version 4.22.5, retrieved on Feb. 3, 2025 at https://online.plantvarieties.eu/ publicConsultation Details?registerId=20241638&denomination=arbel, 2 pp. (Year: 2025).*

* cited by examiner

*Primary Examiner* — June Hwu
(74) *Attorney, Agent, or Firm* — Cassandra Bright

(57) ABSTRACT

A new and distinct cultivar of *Chamelaucium* plant named 'ARBEL' is disclosed, characterized by abundant, small white flowers produced on dense flowering stems. Flower production begins in Spring. Flower buds and the aging receptacle are uniquely colored green- yellow. The new cultivar is a *Chamelaucium*, normally producing cut flower stems, or as a garden or container plant.

2 Drawing Sheets

Figure 1:
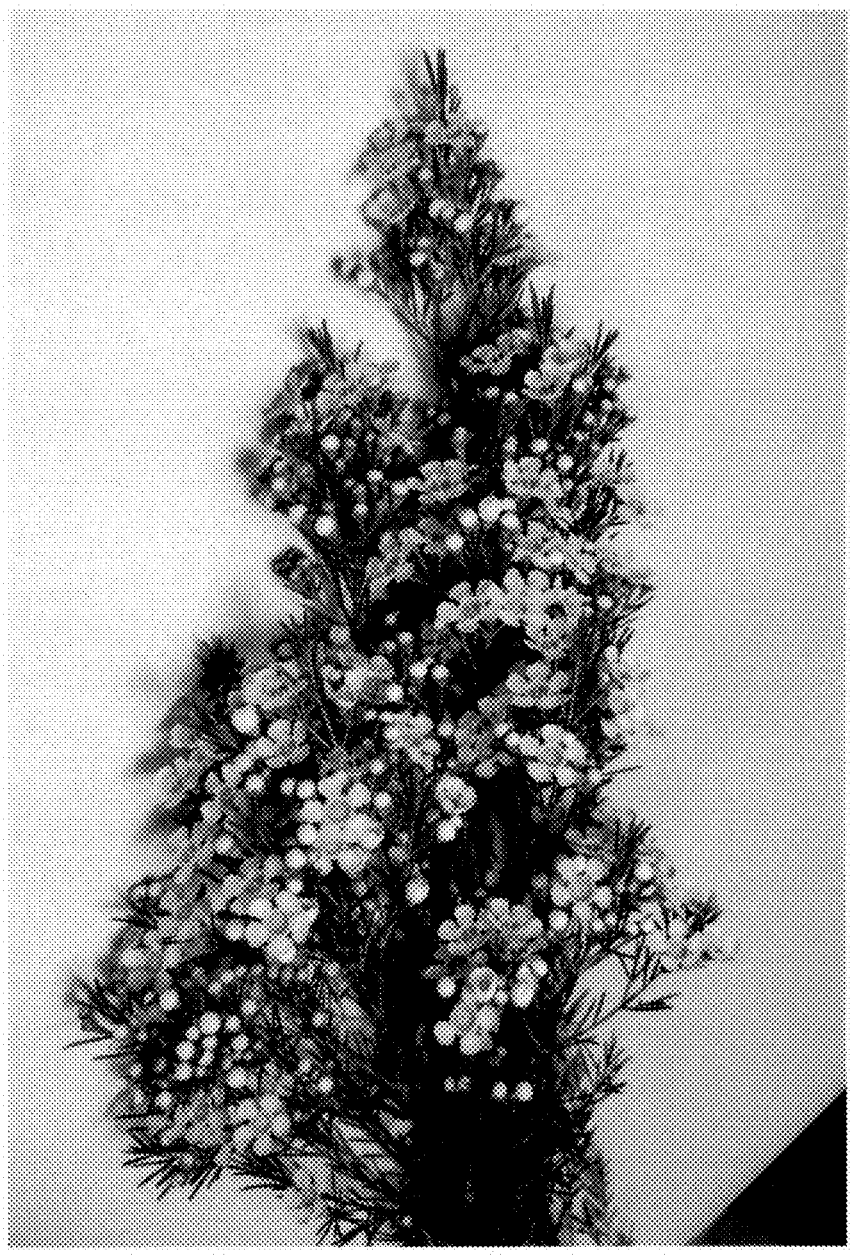

Latin name of the genus and species: *Chamelaucium uncinatum.*
Variety denomination: 'ARBEL'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The crossing resulting in this new cultivar was made in March 2016 at a commercial nursery in Kfar Hess, Israel.

The seed parent is the unpatented cultivar referred to as *Chamelaucium uncinatum* 'Saturn'. The pollen parent is the patented proprietary cultivar referred to as *Chamelaucium uncinatum* 'Titan' U.S. Plant Pat. No. 26,181. The new cultivar was selected in February 2021 by the inventor in a group of seedlings resulting from previously mentioned crossing, in a commercial nursery in Kfar Hess, Israel.

Asexual reproduction of the new cultivar has been performed by terminal vegetative cuttings. This was first performed in November 2021 at a commercial nursery in Kfar Hess, Israel in and has shown that the unique features of this cultivar are stable and reproduced true to type in at least 6 successive generations.

SUMMARY OF THE INVENTION

The cultivar 'ARBEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ARBEL'. These characteristics in combination distinguish 'ARBEL' as a new and distinct *Chamelaucium* cultivar:

1. Spring blooming.
2. Small flower size.
3. White flower color.
4. Yellow-Green flower bud color.
5. Yellow-Green flower aging receptacle color.
6. Dense flowering stem.

PARENT COMPARISON

Plants of the new cultivar 'ARBEL' are similar to plants of the seed parent in most horticultural characteristics, however, plants of the new cultivar 'ARBEL' differ in the following:

1. Aging receptacle color of the new cultivar is yellow-green; receptacle color of the seed parent is purple-brown.
2. Flower color of the new cultivar is white, while the flower color of the seed parent is pink Plants of the new cultivar 'ARBEL' are similar to plants of the pollen parent in most horticultural characteristics, however, plants of the new cultivar 'ARBEL' differ in the following:

1. Aging receptacle color of the new cultivar is yellow-green; receptacle color of the pollen parent is greyed-purple.
2. Flower bud color of the new cultivar is light yellow-green, while the flower bud color of the pollen parent is red-purple.

3. Flower color of the new cultivar is white, while the flower color of the pollen parent is pink

COMMERCIAL COMPARISON

Plants of the new cultivar 'ARBEL' are comparable to the cultivar *Chamelaucium uncinatum* 'Ofir', unpatented. The two *Chamelaucium* cultivars are similar in most horticultural characteristics; however, the new cultivar 'ARBEL' differs in the following:

1. The new cultivar 'Arbel' produces denser flowering stems with many more flowers per stem.
2. The new cultivar blooms in Spring, while this comparator blooms in Winter.

Plants of the new cultivar 'ARBEL' are comparable to the cultivar *Chamelaucium uncinatum* 'Atar', unpatented. The two *Chamelaucium* cultivars are similar in most horticultural characteristics; however, the new cultivar 'ARBEL' differs in the following:

1. The new cultivar has smaller flowers and flower buds than this comparator.
2. The new cultivar blooms in Spring, while this comparator blooms in Winter.
3. The new cultivar 'Arbel' produces denser flowering stems with many more flowers per stem.

BRIEF DESCRIPTION OF THE PHOTOGRAPHS

The accompanying photograph in FIG. 1 illustrates in full color a typical mature flowering stem of 'ARBEL' harvested from a plant of the new cultivar at approximately 1 to 2 years of age.

Figure 2:
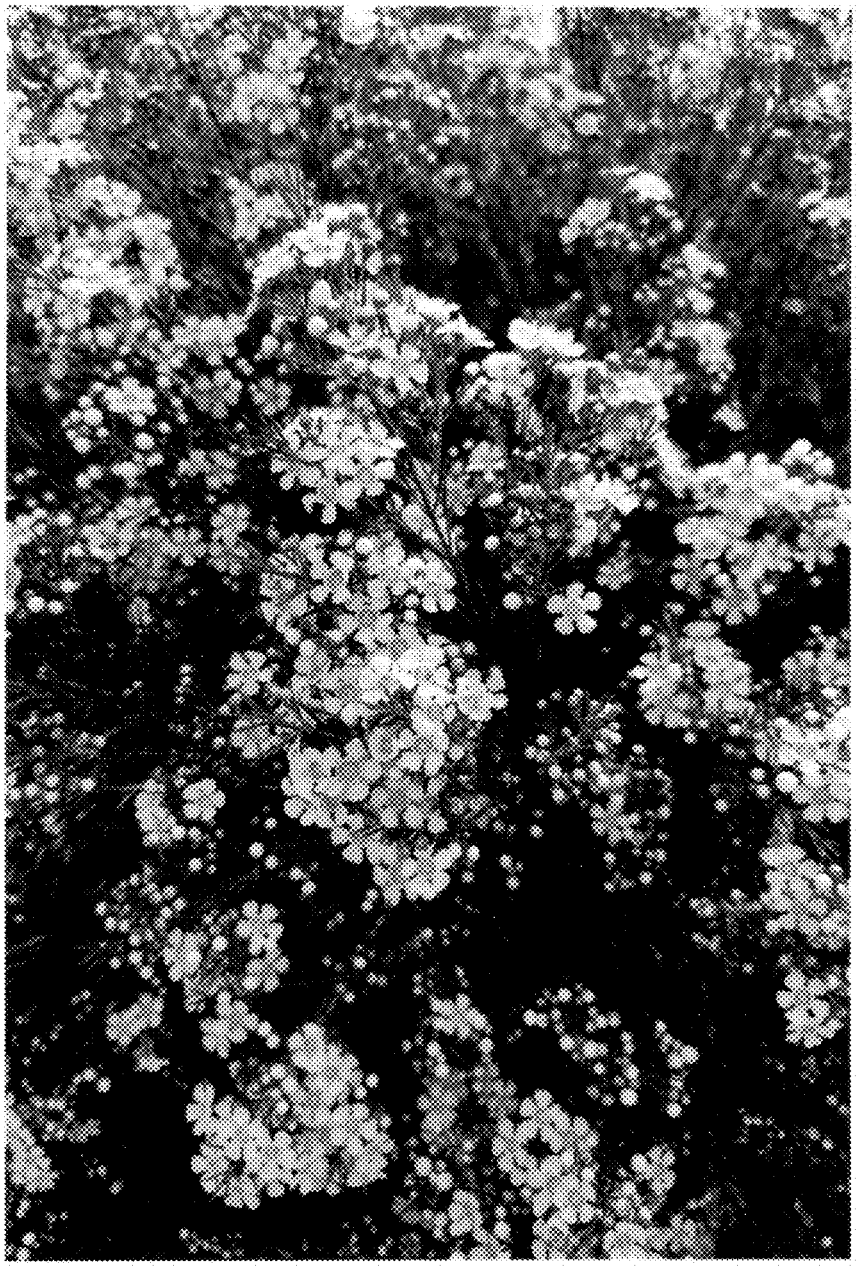

FIG. 2 is a close-up view of flowers on several flowering stems of the new cultivar.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'ARBEL' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'ARBEL'.

Age of plant described: About 1 year old from a rooted cutting.

Typical flowering stems harvested per plant: 100 to 120.

Vase life of flowers: Two weeks.

PROPAGATION

Time to produce a rooted plantlet: 30 to 60 days at approximately 24° C.

Root description: Split root.

PLANT

Growth habit: Upright.

Height: 150 cm to top of flowers.

Plant spread: 120 cm.

Length of primary lateral branches: 60 cm to 150 average.

Diameter of lateral branches: 0.08 to 0.2 cm (branches from the top 30 cm of the primary lateral branch).

Quantity of primary lateral branches: 100 to 120.

Characteristics of primary lateral branches:

*Diameter.*—0.5 cm, measured at 50 cm from top.

*Color.*—Near RHS Brown 200C

*Texture.*—Smooth.

*Strength.*—Low flexibility.

Internode length: Range from 1.5 to 6.5 cm, section of top 30 cm.

FOLIAGE

Leaf:

*Arrangement.*—Opposite.

*Quantity.*—Approximately 8 leaves, in the 5-10 cm section from the top of the branch.

*Average length.*—2.2 cm.

*Average width.*—0.9 mm.

*Shape of blade.*—Needle.

*Shape in cross-section.*—Round.

*Apex.*—Acute.

*Base.*—Truncate.

*Margin.*—Entire.

*Texture.*—Smooth.

*Pubescence.*—None.

*Aspect.*—Straight.

*Color.*—Young foliage, upper side: Near RHS Green 137C. Young foliage, under side: Near RHS Green 137C. Mature foliage, upper side: Near RHS Green 137C. Mature foliage, under side: Near RHS Green 137C.

*Venation.*—Indistinguishable from foliage.

*Petiole.*—Not present.

FLOWER

Natural Flowering season: Spring. Flowering period on the plant lasts about 6 weeks.

Days to flowering from rooted cutting: Photoperiodic conditions. No juvenility.

Individual flower type: 5 petals, about 1.6 cm in diameter.

Location of flowers: Axillary and terminal.

Rate of flower opening: About 50 to 65 days from bud to fully opened flower.

Persistent or self-cleaning: Self-cleaning.

Bud:

*Shape.*—Round.

*Length.*—0.45 cm.

*Diameter.*—0.33 cm.

*Color.*—Near RHS Yellow-Green 150B. As unfurled petals become visible, White 155C.

Flower size:

*Diameter.*—1.7 cm.

*Length.*—0.9 cm.

Corolla:

*Hypanthium shape.*—Obconical

*Petals.*—Arrangement: Free. Rotate hypanthium. Length: 0.6 cm. Diameter: 0.7 cm. Quantity: 5. Texture: Smooth. Apex: Round. Base: Fused.

*Color.*—When opening: Upper surface: Near RHS White 155C. Lower surface: Near RHS White 155C. Fully opened: Upper surface: Near RHS White 155C. Lower surface: Near RHS White 155C.

Aging: Upper surface: Near RHS White 155C. Lower surface: Near RHS White 155C.

Upper surface of receptacle:

*Diameter.*—0.68 cm.

*Length.*—0.17 cm.

*Color.*—When opening: Upper surface: Near RHS Yellow-Green 146C. Lower surface: Near RHS Yellow 12A. Fully opened: Upper surface: Near RHS Yellow-Green 146C. Lower surface: Near RHS Yellow 12A. Aging: Upper surface: Near RHS Yellow-Green 146C. Lower surface: Near RHS Yellow 12A.

Calyx/sepals:

*Quantity per flower.*—5.

*Shape.*—Oval.

*Length.*—0.22 cm. Width: 0.3 cm.

*Margin.*—Smooth. Texture: Smooth. Color: Near RHS Green 137C.

Peduncle: Peduncle consists of the plant stem.

Pedicel:

*Length.*—1.1 cm.

*Diameter.*—0.5 cm.

*Color.*—Near RHS Yellow-Green 144A.

Fragrance: None.

REPRODUCTIVE ORGANS

Stamens:

*Number.*—10.

*Stamen collar color.*—When opening: Yellow-Green 146C. Mature: Yellow-Green 150D.

*Filament length.*—1 mm.

*Filament color.*—RHS White 155C.

Anthers:

*Shape.*—Round.

*Length.*—0.5 mm.

*Color.*—Near RHS Yellow-Orange 22A.

Pollen: Not observed.

Pistil:

*Number.*—1.

*Length.*—0.5 cm.

*Style length.*—0.45 cm.

*Style color.*—Near RHS White 155C.

*Stigma.*—Shape: Round. Color: Near RHS Yellow 4D.

OTHER CHARACTERISTICS

Seeds and fruits: Single flower produces one fruit. When the fruit is fertile, it will produce 1 seed. Fruit and seeds are too small for accurate measurement of characteristics.

Disease/pest resistance: Neither resistance nor susceptibility to the normal diseases and pests of *Chamelaucium* have been observed to date.

Temperature tolerance: From −2° C. to 35° C.

What is claimed is:

1. A new and distinct cultivar of *Chamelaucium* plant named 'ARBEL' as herein illustrated and described.

* * * * *